United States Patent [19]

Jackson et al.

[11] Patent Number: 5,112,600
[45] Date of Patent: May 12, 1992

[54] COMPOSITIONS

[75] Inventors: Robert J. Jackson; Susan A. Duke; Paul Barnett, all of Weybridge, England

[73] Assignee: Beecham Group p.l.c., England

[21] Appl. No.: 701,667

[22] Filed: May 16, 1991

Related U.S. Application Data

[62] Division of Ser. No. 499,712, Mar. 27, 1990, Pat. No. 5,026,539.

[30] Foreign Application Priority Data

Mar. 28, 1989 [GB] United Kingdom ............... 8906913

[51] Int. Cl.$^5$ ........................... A61K 7/16; A61K 7/24
[52] U.S. Cl. ........................................... 424/55; 424/49
[58] Field of Search ........................................ 424/49-58

[56] References Cited

U.S. PATENT DOCUMENTS

| | | | |
|---|---|---|---|
| 4,057,621 | 11/1977 | Pashley et al. | 424/49 |
| 4,645,662 | 2/1987 | Nakashima et al. | 424/52 |
| 5,026,539 | 6/1991 | Jackson et al. | 424/49 |

FOREIGN PATENT DOCUMENTS

| | | |
|---|---|---|
| 188313 | 7/1986 | European Pat. Off. |
| 242977 | 3/1987 | European Pat. Off. |
| 935441 | 6/1948 | France |
| 2188548 | 10/1987 | United Kingdom |

OTHER PUBLICATIONS

Duke et al. CA. 109:215748e (1988) of Caries Res. 22(6):350-2 (1988).
Duke et al. CA. 105:120543n (1986) of EP 188 313 23 Jul. 1986 14 pp.
Pashley et al. CA. 102:31929p (1985) of J. Peurdent, 55(9):522-5 (1984).
Pashley et al. CA. 88:55104j (1978) of U.S. 4,057,621 8 Nov. 77.
Lion Corp. CA. 102:172445g (1985) of JPN 6004117 10 Jan. 1985.
Schott et al. CA. 101:157538h (1984) of J. Pharm. Sci. 73(6), 793-9 (1984).
Just et al. CA. 88:8865y (1978) of Ger. Ofc. 2,615,698 20 Oct. 1977.

Primary Examiner—Shep K. Rose
Attorney, Agent, or Firm—Rosenman & Colin

[57] ABSTRACT

An anti-caries composition has a source of hydrogen citrate ions, preferably an alkali metal hydrogen citrate salt, an oxalate salt and an orally acceptable excipient, and optionally further comprises an ionic fluorine-containing compound. The composition may be in the form of dentifrice when silica is the preferred abrasive, or a mouthwash.

13 Claims, No Drawings

COMPOSITIONS

CROSS-REFERENCE

This is a division of Ser. No. 499,712 filed Mar. 27, 1990, now U.S. Pat. No. 5,026,539.

The present invention relates to oral hygiene compositions, and in particular to compositions having improved anti-caries activity.

The use of alkali metal fluorides and alkali metal monofluorophosphates as anti-caries agents is well established. It has also been proposed that the anti-caries efficacy of compositions comprising fluoride may be enhanced by incorporating either hydrogen citrate ions (EP-A-O-188 313, Beecham Group p.l.c.) or oxalate ions (GB-A-2 188 548; Beecham Group p.l.c.) into the composition.

It has now been found that anti-caries activity may be achieved, even in the absence of fluoride, when a combination of oxalate ions and hydrogen citrate ions is used, within a specific pH range.

Accordingly, the present invention provides an oral hygiene composition comprising:
(a) up to 10% by weight of a source of hydrogen citrate ions; (b) up to 7% by weight of an oxalate salt; and
(c) an orally acceptable excipient;
the composition having a pH of from 4 to 7.

Preferably the source of hydrogen citrate ions is a soluble alkali metal salt, such as disodium hydrogen citrate.

It will be readily appreciated that hydrogen citrate ions may also be provided by a dihydrogen citrate salt and/or a citrate salt, the dihydrogen citrate and/or citrate ions being converted to hydrogen citrate ions in consequence of the pH of the composition of the invention.

Preferably, the source of hydrogen citrate ions is present in an amount of from 0.025 to 10%, more preferably from 0.1 to 4%, by weight of the composition.

Preferably the oxalate salt is an alkali metal oxalate and/or an alkaline earth metal oxalate, and may also be a mixture of one or more alkali metal oxalates and/or alkaline earth metal oxalates. Suitable oxalates for use in compositions of the invention include soluble and sparingly soluble oxalates such as sodium, potassium, lithium, calcium, magnesium, barium and strontium oxalate. Particularly preferred oxalates are sodium oxalate, potassium oxalate and calcium oxalate or mixtures thereof.

Preferably the oxalate salt is present in an amount of from 0.0025 to 7%, more preferably from 0.05 to 3%, by weight of the composition.

In a further aspect of the invention, oral hygiene compositions may further comprise an ionic fluorine-containing compound, to provide additional anti-caries activity.

The ionic fluorine-containing compound may be a fluoride salt, preferably an alkali-metal fluoride. Sodium fluoride is especially preferred but the corresponding potassium and/or lithium salts can also be employed. Other suitable fluoride salts include ammonium fluoride, tin (II) fluoride and zinc fluoride.

In addition to, or instead of, the above fluoride salts, the ionic fluorine-containing compound may also comprise a monofluorophosphate, preferably an alkali metal monofluorophosphate. Sodium monofluorophosphate is especially preferred but the corresponding potassium and/or lithium salts can also be employed. Other suitable monofluorophosphates include monofluoropolyphosphate salts, for instance compounds of the formulae $Na_4P_3O_9F$; $K_4P_3O_9F$; $Na_3KP_3O_9F$; $(NH_4)_3NaP_3O_9F$; and $Li_4P_3O_9F$.

The total amount of fluoride and/or monofluorophosphate used is to some extent dependent on the type of oral hygiene composition, but it should be an effective, but non-toxic, amount.

Typically the ionic fluorine-containing compound(s) is present in an amount to provide a total of from 0.01 to 0.25% of fluorine, preferably 0.025 to 0.15%, based on the weight of the composition.

Preferably, the weight ratio of ionic fluorine-containing compound(s) to hydrogen citrate ions is from 1:10 to 1:500, more preferably 1:50 to 1:250.

The compositions of the invention may optionally contain other agents known to enhance the anticaries effect of fluoride and monofluorophosphate, for instance, calcium glycerophosphate (which is known to enhance the anticaries efficacy of monofluorophosphate); this being incorporated in a weight ratio of up to 1:3, preferably 1:20 to 1:3, compared to the total weight of monofluorophosphate salt.

The compositions of the invention may be presented in the form of a conventional dentifrice, for instance a toothpaste or a dental powder formulation or as a conventional mouthwash. The compositions may also be in the form of other oral hygiene compositions, for instance, the ingredients may be incorporated into compositions which will be chewed by the user, for instance, chewing gum, tablets, pastilles and lozengers.

A dentifrice according to the invention preferably includes in the orally acceptable excipient, a dentally acceptable abrasive, the choice of abrasive only be limited to the requirement to keep the pH of the final composition below 7. Thus, calcium carbonate, which has been found to give a composition pH above 7, would not be suitable for use in the present invention. Examples of suitable abrasives include dicalcium phosphate, calcium pyrophosphates, alumina, aluminium hydroxide, pumice, plastics particles, zinc orthophosphate and silica.

The abrasive is typically present in the range from 5 to 75%, preferably 10 to 50%, by weight of the composition.

Advantageously the abrasive is silica which may be a natural amorphous silica, for instance, diatomaceous earth, or a synthetic amorphous silica, for instance a precipitated silica or a silica gel, such as the silica xerogels described in U.S. Pat. No. 3,538,230.

Preferred precipitated silicas are those marketed under the trade marks ZEODENT and TIOXOSIL by J. M. Huber Corporation and Rhone-Poulenc, respectively.

The compositions of the invention will also usually contain as excipients surfactants, gelling agents, humectants and other ingredients such as flavouring, sweetening and colouring agents.

Surfactants used in the composition of the invention are normally water-soluble, non-soap, or synthetic organic detergents. Suitable surfactants include the water-soluble salts of: higher fatty acid monoglyceride monosulphates (for example sodium hydrogenated coconut fatty acid monoglyceride monosulphate), higher alkyl sulphates (for example sodium lauryl sulphate), alkylarylsulphonates (for example sodium dodecylbenzenesulphonates), and higher alkyl sulphoacetates (for instance sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amides of glycine, sarcosine, alanine, 3-aminopropanoic acid and valine, particularly the N-lauroyl, myristoyl and palmitoyl sarcosinate compounds. Low ionic surfactants such as sodium N-methyl-N-cocoyl laurate, which is marketed under the trade mark ADINOL CT by Croda, are also suitable. Conventional non-ionic surfactants may also be included, if desired, for instance, condensates of propylene glycol and polyethoxylated hydrogenated castor oil such as a cremaphor.

The surfactants are generally present in an amount of 0.05 to 15%, preferably 0.05 to 5% by weight of the composition.

Humectants suitable for use in compositions of the invention include glycerol, sorbitol and/or a glycol, including suitable mixtures thereof. Suitably, the glycol is propylene glycol or a polyethylene glycol such as PEG 300.

It is also preferred to use in a composition of the invention which is in the form of a toothpaste a gelling agent such as a natural or synthetic gum or gum-like material. Whilst a non-ionic gum such as guar gum or xanthan gum is particularly preferred, another gum or gum-like material, such as Irish Moss, gum tragacanth, sodium carboxymethyl cellulose, polyvinylpyrrolidone, starch or a thickening silica may also be used. The gelling agent content is usually from 0.001 to 10%, preferably 0.01 to 5% by weight of the composition.

Other materials may be added such as sweetening agents (e.g. soluble saccharin), flavouring oils (e.g. oils of spearmint, wintergreen, peppermint, menthol), chloroform, colouring or whitening agents (e.g. titanium dioxide), preservative (e.g. sodium benzoate), emulsifying agents, silicones, alcohol, chlorophyll compounds (e.g. sodium copper chlorophyllin), antibacterial agents (e.g. triclosan, chlorhexidine), antiplaque agents and anti-calculus agents.

If necessary and required, compositions of the invention may include water.

Oral hygiene compositions according to the invention may be prepared in a conventional manner by admixture of the ingredients in the required proportions in any order that is convenient and thereafter and if necessary adjusting the pH. Thus, the ingredients may be mixed in the dry state or as slurries or solutions.

A mouthwash according to the invention may be presented for use as a conventional gargle and may also be packaged in a suitable delivery device for use as a mouth spray.

In another aspect, the invention also provides a method of preventing or treating caries which method comprises the application of an effective amount of a composition according to the invention to the oral cavity.

Oral hygiene compositions of the present invention have been found to inhibit glucose utilisation and lactic acid production by microorganisms found in the oral cavity and this appears to be the mechanism by which the improved anti-caries effect of the compositions is achieved The invention is illustrated by the following examples.

EXAMPLE 1

| Mouthwash | % |
|---|---|
| Disodium hydrogen citrate | 0.10 |
| Sodium oxalate | 0.30 |
| Ethanol | 10.00 |
| Glycerol | 5.00 |
| Flavour | 0.12 |
| Polyethoxylated hydrogenated castor oil derivative* | 0.20 |
| Sodium saccharin | 0.05 |
| Soluble dyes | q.s. |
| Deionized water to | 100.00 |

EXAMPLE 2

| Gel Toothaste | % |
|---|---|
| Sorbitol 70% solution | 50.00 |
| Sodium carboxymethyl cellulose | 1.00 |
| Polyethylene glycol (PEG 300) | 3.00 |
| Thickening silica | 2.50 |
| Abrasive silica | 16.00 |
| Flavour | 0.80 |
| Sodium saccharin | 0.30 |
| Disodium hydrogen citrate | 0.40 |
| Sodium oxalate | 1.20 |
| Soluble dyes | q.s. |
| Sodium lauryl sulphate | 1.70 |
| Sodium fluoride | 0.23 |
| Water to | 100.00 |

*A condensate of propylene glycol and polyethoxylated hydrogenated castor oil.

TEST DATA

Effect on the pH of Dental Plaque

Following the methodology of Duke, S. A., Caries Research, 1986, 20 (3), 278, subjects (n=18) used a test composition in the form of a mouthwash for 1 week ab lib. They then refrained from all oral hygiene measures for 24 hours.

On the test day, each subject refrained from eating or drinking for 1 hour prior to and during the test period. Each subject rinsed his mouth with the test mouthwash (10 ml).

After 30 minutes, plaque samples were collected from the molars and premolars of each subject and the mouth then rinsed with aqueous sucrose (10% w/v, 10 ml).

After another 10 minutes, plaque samples were again taken from the molars and premolars of each subject.

Each plaque sample was immediately suspended in physiological saline (20 μl) and the pH measured using a microcombination electrode. The results are presented in the Table.

| Composition* | Plaque pH after aqueous sucrose treatment |
|---|---|
| (a) Water | 5.46 ± 0.18 |
| (b) Disodium hydrogen citrate (0.1%) | 5.60 ± 0.23 |
| (c) Sodium oxalate (0.3%) | 5.73 ± 0.21 |
| (d) Disodium hydrogen citrate (0.1%) and sodium oxalate | 6.14 ± 0.16 |

| Composition* | Plaque pH after aqueous sucrose treatment |
|---|---|
| (0.3%) | | composition (d) superior to compositions (a), (b) or (c), p < 0.001;
composition (b) superior to composition. (a) p < 0.02;
composition (c) superior to composition. (a) p < 0.001.
*The pH of each composition was adjusted to pH 5.5.

CONCLUSIONS

The data presented in the table shows that whilst each of hydrogen citrate and oxalate have a statistically significant effect on the post sucrose challenge plaque pH, in combination, hydrogen citrate and oxalate have an effect which is statistically superior to that given by either alone.

We claim:

1. An oral hygiene composition in the form of a non-fluoride mouthwash, comprising:
   (a) greater than 0 to 10% by weight of a source of hydrogen citrate ions;
   (b) greater than 0 to 7% by weight of an oxalate salt; and
   (c) an orally acceptable excipient;
the composition having a pH of from 4 to 7 and containing no fluoride anti-caries agent.

2. A mouthwash according to claim 1 wherein the source of hydrogen citrate ions is a soluble alkali metal salt.

3. A mouthwash according to claim 2 wherein the salt is a hydrogen citrate salt.

4. A mouthwash according to claim 1 wherein the source of hydrogen citrate ions is present in an amount of from 0.025 to 10% by weight of the composition.

5. A mouthwash according to claim 1 wherein the oxalate salt is an alkali metal oxalate or an alkaline earth metal oxalate, or a combination thereof 6. A mouthwash according to claim 1 wherein the oxalate salt is present in an amount of from 0.0025 to 7% by weight of the composition.

7. A method of preventing or treating caries which method comprises the application to a subject of an effective amount of a mouthwash of claim 1 to the oral cavity.

8. An oral hygiene composition in the form of a non-fluoride mouthwash, comprising:
   (a) greater than 0 to 10% by weight of a source of hydrogen citrate ions wherein said source is a soluble alkali metal salt;
   (b) greater than 0 to 7% by weight of an oxalate salt; and
   (c) an orally acceptable excipient;
the composition having a pH of from 4 to 7 and containing no fluoride anti-caries agent.

9. A mouthwash according to claim 8 wherein the alkali metal salt is a hydrogen citrate salt.

10. A mouthwash according to claim 8 wherein the source of hydrogen citrate ions is present in an amount of from 0.025 to 10% by weight of the composition.

11. A mouthwash according to claim 8 wherein the oxalate salt is an alkali metal oxalate or an alkaline earth metal oxalate, or a combination thereof.

12. A mouthwash according to claim 8 wherein the oxalate salt is present in an amount of from 0.0025 to 7% by weight of the composition.

13. A method of preventing or treating caries which method comprises the application to a subject of an effective amount of a mouthwash of claim 8 to the oral cavity.

* * * * *